(12) United States Patent
Quallich et al.

(10) Patent No.: US 7,094,930 B2
(45) Date of Patent: Aug. 22, 2006

(54) PHARMACEUTICALLY ACCEPTABLE SALTS OF SERTRALINE AND PHARMACEUTICAL COMPOSITIONS THEREOF

(75) Inventors: George J. Quallich, North Stonington, CT (US); Lewin T. Wint, Wilmette, IL (US)

(73) Assignee: Pfizer Inc, New York, NY (US)

( * ) Notice: Subject to any disclaimer, the term of this patent is extended or adjusted under 35 U.S.C. 154(b) by 269 days.

(21) Appl. No.: 10/763,768

(22) Filed: Jan. 22, 2004

(65) Prior Publication Data

US 2004/0198818 A1    Oct. 7, 2004

Related U.S. Application Data

(60) Provisional application No. 60/442,089, filed on Jan. 23, 2003.

(51) Int. Cl.
*C07C 211/42*    (2006.01)
*A61K 31/135*    (2006.01)

(52) U.S. Cl. ............................ 564/308; 514/647
(58) Field of Classification Search ............... 564/308
See application file for complete search history.

(56) References Cited

U.S. PATENT DOCUMENTS 6,495,721 B1    12/2002    Schwartz
6,723,878 B1 *    4/2004    Laitinen ............... 564/308

FOREIGN PATENT DOCUMENTS

WO    WO9901121    1/1999
WO    WO0021521    4/2000

OTHER PUBLICATIONS

Julius F. Remenar et al.: "Salt Selection and Simultaneous Polymorphism Assessment via High Throughput Crystallization: The Case of Sertraline"; Organic Process Research and Development, vol. 7, No. 6, Oct. 14, 2003, pp. 990-996; XP002277129 the whole document.

* cited by examiner

*Primary Examiner*—Brian Davis
(74) *Attorney, Agent, or Firm*—Steve T. Zelson; A. David Joran

(57) ABSTRACT

The present invention is directed to certain pharmaceutically acceptable salts of the therapeutically potent selective serotonin reuptake inhibitor, sertraline:

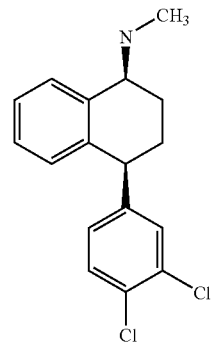

and pharmaceutical compositions thereof, wherein said salts are selected from the group consisting of the p-toluenesulfonic acid salt, the fumaric acid salt, the benzenesulfonic acid salt, the benzoic acid salt, the L-tartaric acid salt and the (−)-camphor-10-sulfonic acid salt.

20 Claims, 12 Drawing Sheets

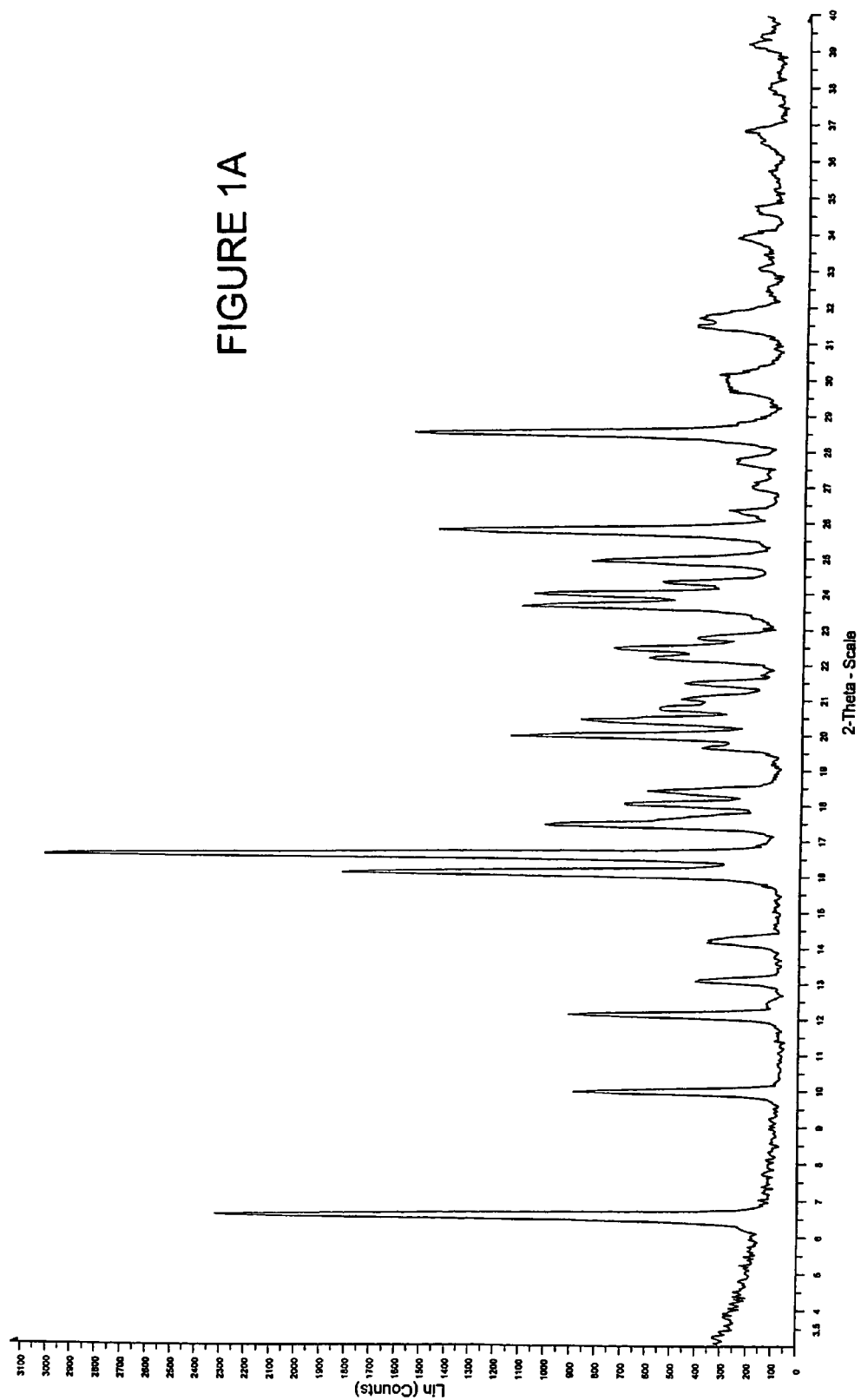

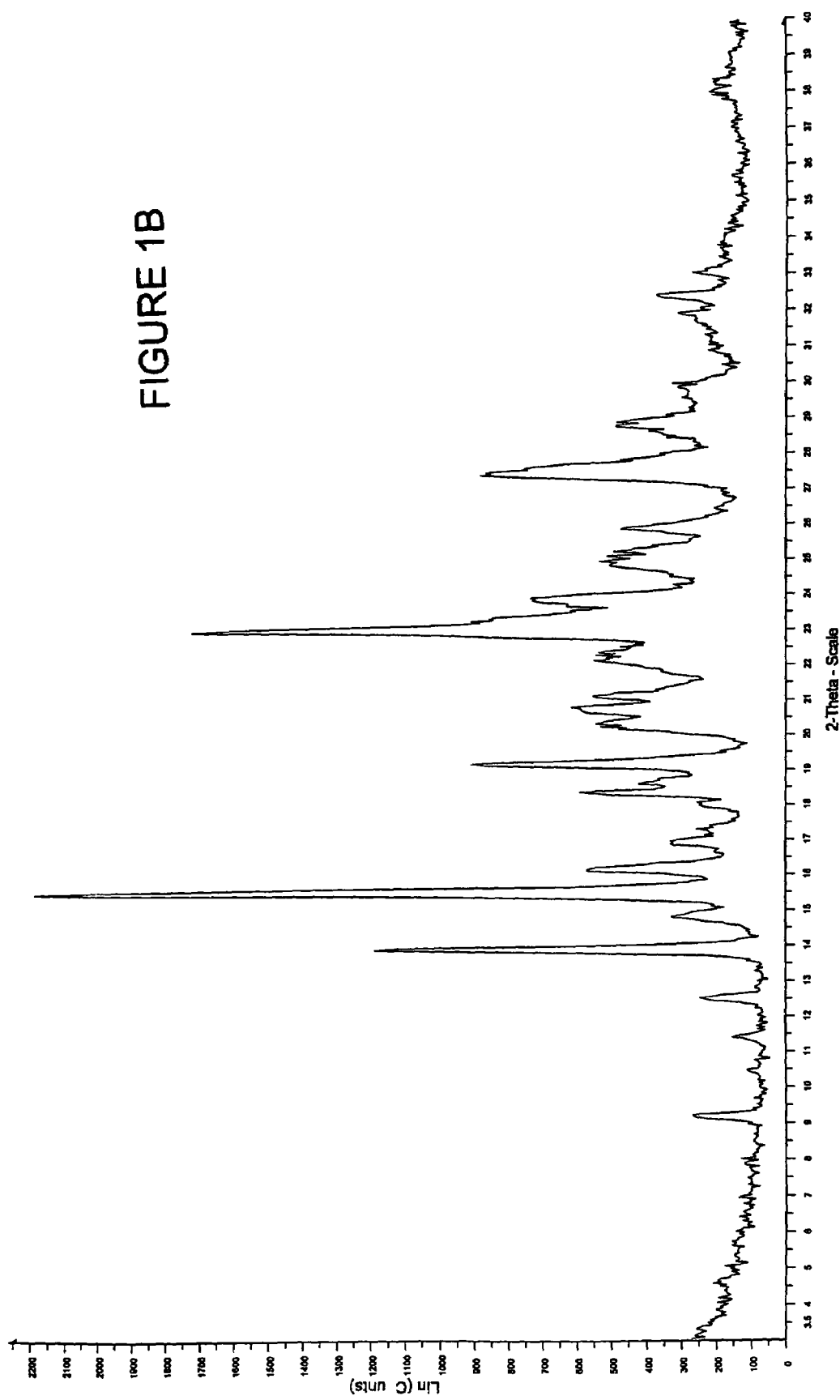

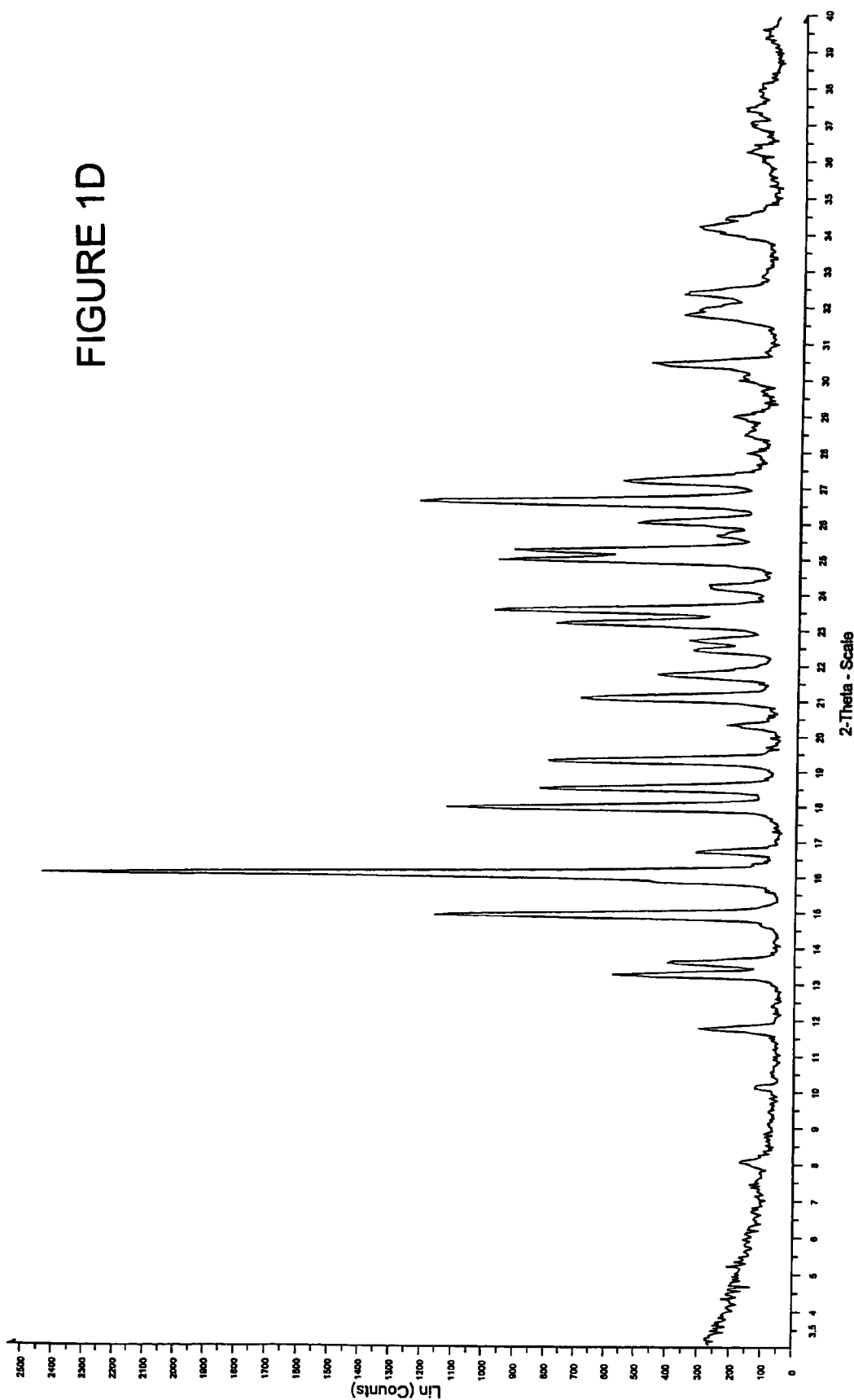

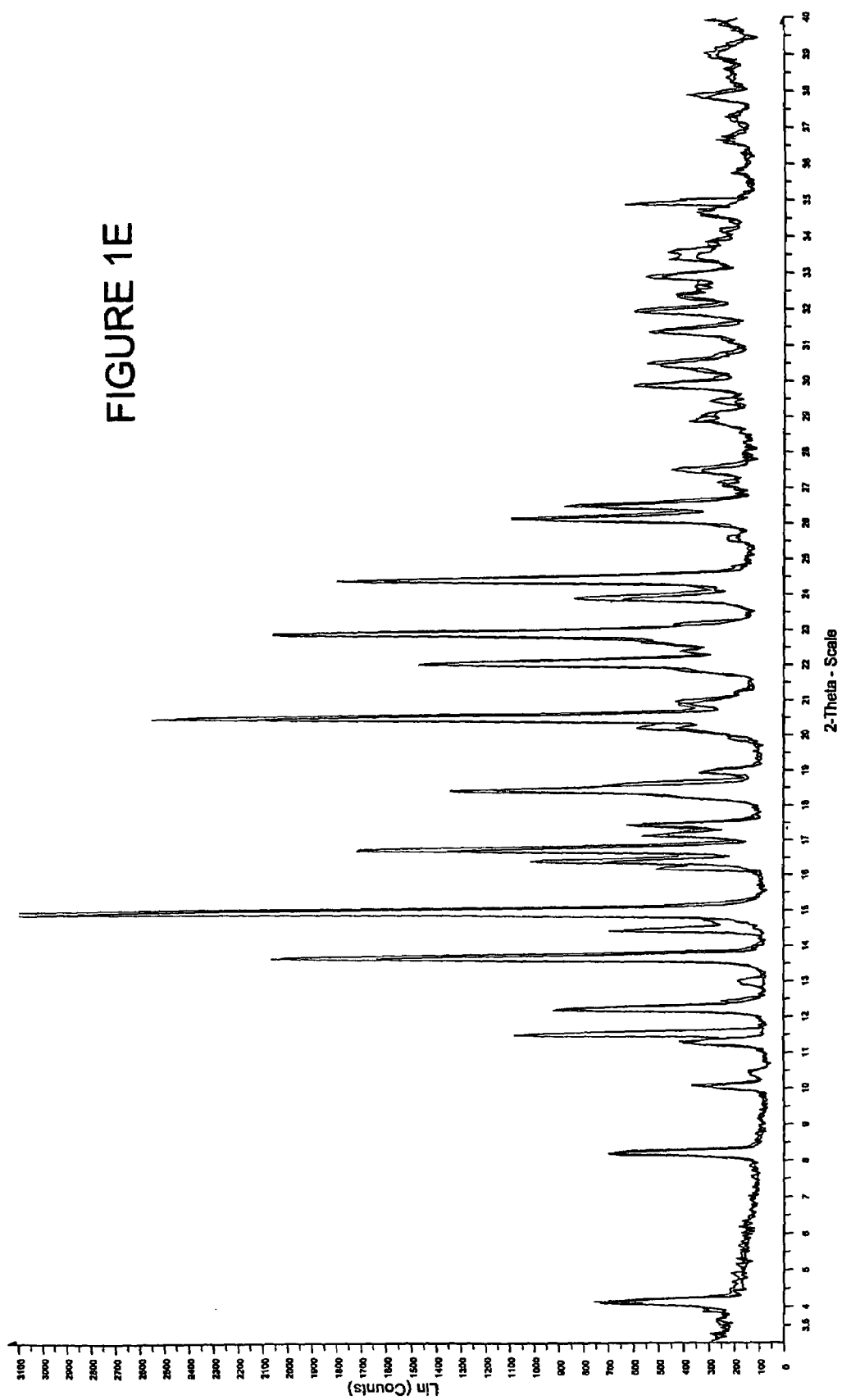

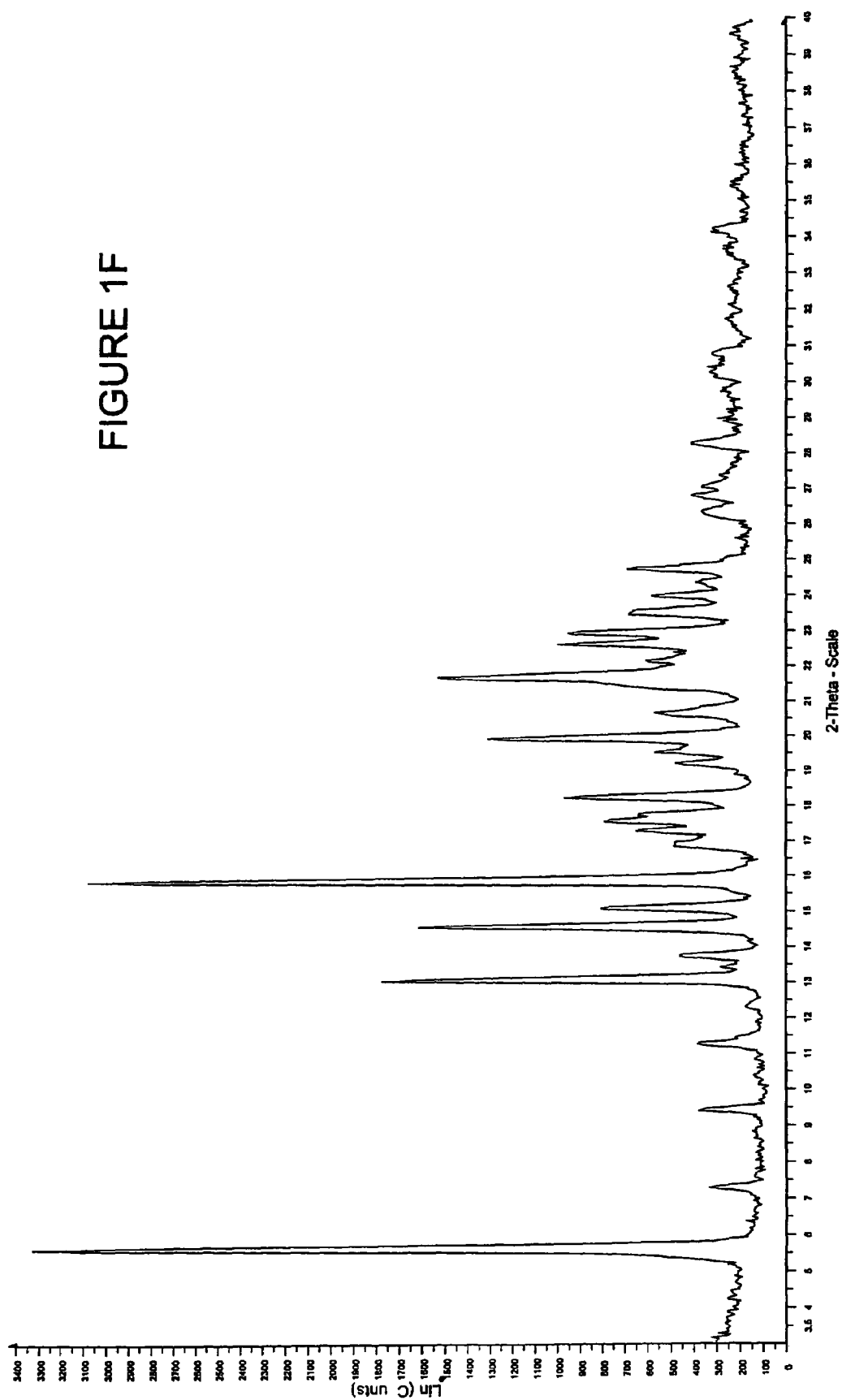

PHARMACEUTICALLY ACCEPTABLE SALTS OF SERTRALINE AND PHARMACEUTICAL COMPOSITIONS THEREOF

This application claims the benefit of U.S. Provisional Patent Application Ser. No. 60/442,089, filed Jan. 23, 2003.

The present invention is directed to certain pharmaceutically acceptable salts of sertraline:

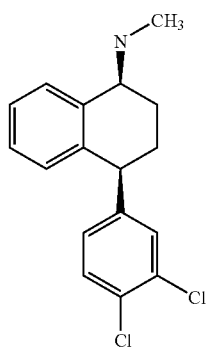

and pharmaceutical compositions thereof, wherein said salts are selected from the group consisting of the p-toluenesulfonic acid salt, the fumaric acid salt, the benzenesulfonic acid salt, the benzoic acid salt, the L-tartaric acid salt and the (−)-camphor-10-sulfonic acid salt.

The compound, sertraline, or (1S-cis)-4-(3,4-dichlorophenyl)-1,2,3,4-tetrahydro-N-methyl-1-naphthylenamine, is a therapeutically potent selective serotonin reuptake inhibitor. This compound is useful for the treatment of a number of diseases, disorders and conditions associated with the central nervous system and the modulation of serotonin receptors.

Sertraline is commercially sold as its hydrochloride salt. U.S. Pat. No. 4,536,518 describes the synthesis of certain cis-4-phenyl-1,2,3,4-tetrahydronaphthalenamine derivatives, including sertraline and generally recites pharmaceutically acceptable salts of these compounds. U.S. Pat. No. 5,248,699 describes several polymorphs of sertraline hydrochloride. The foregoing applications, owned in common with the present application and incorporated herein by reference in their entirety, generically recite pharmaceutically acceptable acid addition salts for the compounds referred to therein.

The salts of the present invention exhibit properties, including those of solid-state stability and compatibility with certain drug product formulation excipients, that render them preferable in comparison to the free base and other known salts of sertraline.

SUMMARY OF THE INVENTION

The present invention is directed to pharmaceutically acceptable salts of sertraline:

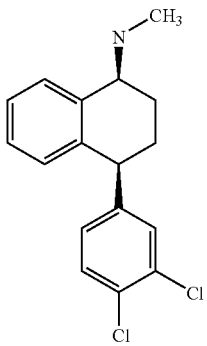

wherein said salts are selected from the group consisting of the p-toluenesulfonic acid salt, the fumaric acid salt, the benzenesulfonic acid salt, the benzoic acid salt, the L-tartaric acid salt and the (−)-camphor-10-sulfonic acid salt.

In one preferred embodiment of the invention, the pharmaceutically acceptable salt is the p-toluenesulfonic acid salt and hydrates thereof. The p-toluenesulfonic acid salt of sertraline is characterized by the principal x-ray diffraction pattern peaks expressed in terms of 2θ and d-spacings (also referred to as d-value) measured with copper radiation (within the margins of error indicated):

| Angle 2θ (±0.2) | d-value (Å) (±0.2) |
|---|---|
| 6.5 | 13.6 |
| 16.1 | 5.5 |
| 16.6 | 5.3 |
| 20.0 | 4.4 |
| 23.7 | 3.8 |
| 24.0 | 3.7 |
| 25.8 | 3.5 |
| 28.5 | 3.1 |

The sertraline p-toluenesulfonic acid salt crystal is characterized in that it generally forms plates. The sertraline p-toluenesulfonic acid salt is further characterized in having an onset of melting transition/decomposition point at about 260° C. as measured by differential scanning calorimetry. Further, the sertraline p-toluenesulfonic acid salt of the invention is also characterized in having an aqueous solubility of 0.4 mg/ml and a pH of 4.1 in aqueous solution. In addition, the sertraline p-toluenesulfonic acid salt has a hygroscopicity of approximately 0.1% at 90% relative humidity.

In another preferred embodiment of the invention, the pharmaceutically acceptable salt is the fumaric acid salt. The fumaric acid salt of sertraline is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 13.9 | 6.4 |
| 15.5 | 5.7 |
| 18.3 | 4.8 |
| 19.1 | 4.6 |
| 20.8 | 4.3 |

-continued

| Angle 2θ (±0.2) | d-value (Å) (±0.2) |
|---|---|
| 23.0 | 3.9 |
| 23.4 | 3.8 |
| 27.4 | 3.2 |

The sertraline fumaric acid salt is further characterized in having an onset of melting transition at about 187° C. as measured by differential scanning calorimetry. Further, the sertraline fumaric acid salt of the invention is also characterized in having an aqueous solubility of 2.8 mg/ml and a pH of 3.4 in aqueous solution. In addition, the sertraline fumaric acid salt has a hygroscopicity of approximately 0.3% at 90% relative humidity.

In another preferred embodiment of the invention, the pharmaceutically acceptable salt is the benzenesulfonic acid salt. The benzenesulfonic acid salt of sertraline is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 7.5 | 11.9 |
| 15.1 | 5.9 |
| 22.4 | 4.0 |
| 22.9 | 3.9 |
| 23.4 | 3.8 |
| 24.4 | 3.6 |
| 24.8 | 3.6 |
| 27.9 | 3.2 |

The sertraline benzenesulfonic acid salt crystal is characterized in that it generally forms needles. The sertraline benzenesulfonic acid salt is further characterized in having a solid-solid transition at about 185° C. and an onset of melting transition point at about 230° C. as measured by differential scanning calorimetry. Further, the sertraline benzenesulfonic acid salt of the invention is also characterized in having an aqueous solubility of 0.9 mg/ml and a pH of 4.6 in aqueous solution. In addition, the sertraline benzenesulfonic acid salt has a hygroscopicity of approximately 0.3% at 90% relative humidity.

In a preferred embodiment of the invention, the pharmaceutically acceptable salt is the benzoic acid salt. The benzoic acid salt of sertraline is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 14.9 | 5.9 |
| 16.1 | 5.5 |
| 18.0 | 4.9 |
| 18.5 | 4.8 |
| 19.3 | 4.6 |
| 23.6 | 4.4 |
| 25.0 | 3.6 |
| 25.2 | 3.5 |

The sertraline benzoic acid salt is further characterized in having an onset of melting transition point at about 154° C. as measured by differential scanning calorimetry. Further, the sertraline benzoic acid salt of the invention is also characterized in having an aqueous solubility of 0.52 mg/ml and a native pH of 5.2 in aqueous solution. In addition, the sertraline benzoic acid salt has a hygroscopicity of approximately 0.1% at 100% relative humidity.

In a preferred embodiment of the invention, the pharmaceutically acceptable salt is the L-tartaric acid salt. The L-tartaric acid salt of sertraline is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 13.7 | 6.5 |
| 15.0 | 5.9 |
| 16.7 | 5.3 |
| 18.4 | 4.8 |
| 20.5 | 4.3 |
| 22.1 | 4.0 |
| 22.9 | 3.9 |
| 24.5 | 3.6 |

The sertraline L-tartaric acid salt is further characterized in having an onset of melting transition/decomposition point at about 184° C. as measured by differential scanning calorimetry. Further, the sertraline L-tartaric acid salt of the invention is also characterized in having an aqueous solubility of 4.8 mg/ml and a pH of 3.0 in aqueous solution. In addition, the sertraline L-tartaric acid salt has a hygroscopicity of less than 0.1% at 100% relative humidity.

In a preferred embodiment of the invention, the pharmaceutically acceptable salt is the (−)-camphor-10-sulfonic acid salt. The (−)-camphor-10-sulfonic acid salt of sertraline is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 5.6 | 15.8 |
| 13.1 | 6.8 |
| 14.6 | 6.1 |
| 15.8 | 5.6 |
| 18.2 | 4.9 |
| 19.9 | 4.5 |
| 21.7 | 4.1 |
| 22.6 | 3.9 |

The sertraline (−)-camphor-10-sulfonic acid salt is further characterized in having an onset of melting transition/decomposition point at about 265° C. as measured by differential scanning calorimetry. Further, the sertraline (−)-camphor-10-sulfonic acid salt of the invention is also characterized in having an aqueous solubility of 1.5 mg/ml and a native pH of 4.6 in aqueous solution. In addition, the sertraline, (−)-camphor-10-sulfonic acid salt has a hygroscopicity of approximately 0.4% at 100% relative humidity.

Another embodiment of the invention relates to a pharmaceutical composition comprising a salt of sertraline selected from the p-toluenesulfonic acid salt, the fumaric acid salt, the benzenesulfonic acid salt, the benzoic acid salt, the L-tartaric acid salt and the (−)-camphor-10-sulfonic acid salt; a pharmaceutically acceptable carrier or excipient, for use in the treatment in a mammal a disease, disorder or condition selected from the group consisting of aggression disorders; anxiety disorders (e.g., panic attack, agoraphobia, panic disorder with or without agoraphobia, agoraphobia without history of panic disorder, specific phobia, social phobia, obsessive-compulsive disorder, post-traumatic stress disorder and acute stress disorder); cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit-hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders) and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g., intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified disorders); and vision disorders, including glaucoma.

The present invention further relates to a method of treating in a mammal a disease, disorder or condition selected from the group consisting of aggression disorders; anxiety disorders (e.g., panic attack, agoraphobia, panic disorder with or without agoraphobia, agoraphobia without history of panic disorder, specific phobia, social phobia, obsessive-compulsive disorder, post-traumatic stress disorder and acute stress disorder); cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit/hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders)

and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g., intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified disorders); and vision disorders, including glaucoma; comprising administering to a subject in need thereof a therapeutically effective amount of a salt of sertraline selected from the group consisting of the p-toluenesulfonic acid salt, the fumaric acid salt, the benzenesulfonic acid salt, the benzoic acid salt, the L-tartaric acid salt and the (−)-camphor-10-sulfonic acid salt.

BRIEF DESCRIPTION OF THE DRAWINGS

FIG. 1A is the observed powder X-ray diffraction pattern of the p-toluenesulfonic acid salt of sertraline (y axis is linear counts per second; X in degrees 2 theta).

FIG. 1B is the observed powder X-ray diffraction of the fumaric acid salt of sertraline (y axis is linear counts per second; X in degrees 2 theta).

FIG. 1D is the observed powder X-ray diffraction of the benzoic acid salt of sertraline (y axis is linear counts per second; X in degrees 2 theta).

FIG. 1E is the observed powder X-ray diffraction pattern of the L-tartaric acid salt of sertraline (y axis is linear counts per second; X in degrees 2 theta).

FIG. 1F is the observed powder X-ray diffraction of the (−)-camphor-10-sulfonic acid salt of sertraline (y axis is linear counts per second; X in degrees 2 theta).

DETAILED DESCRIPTION OF THE INVENTION

Figure 1C:
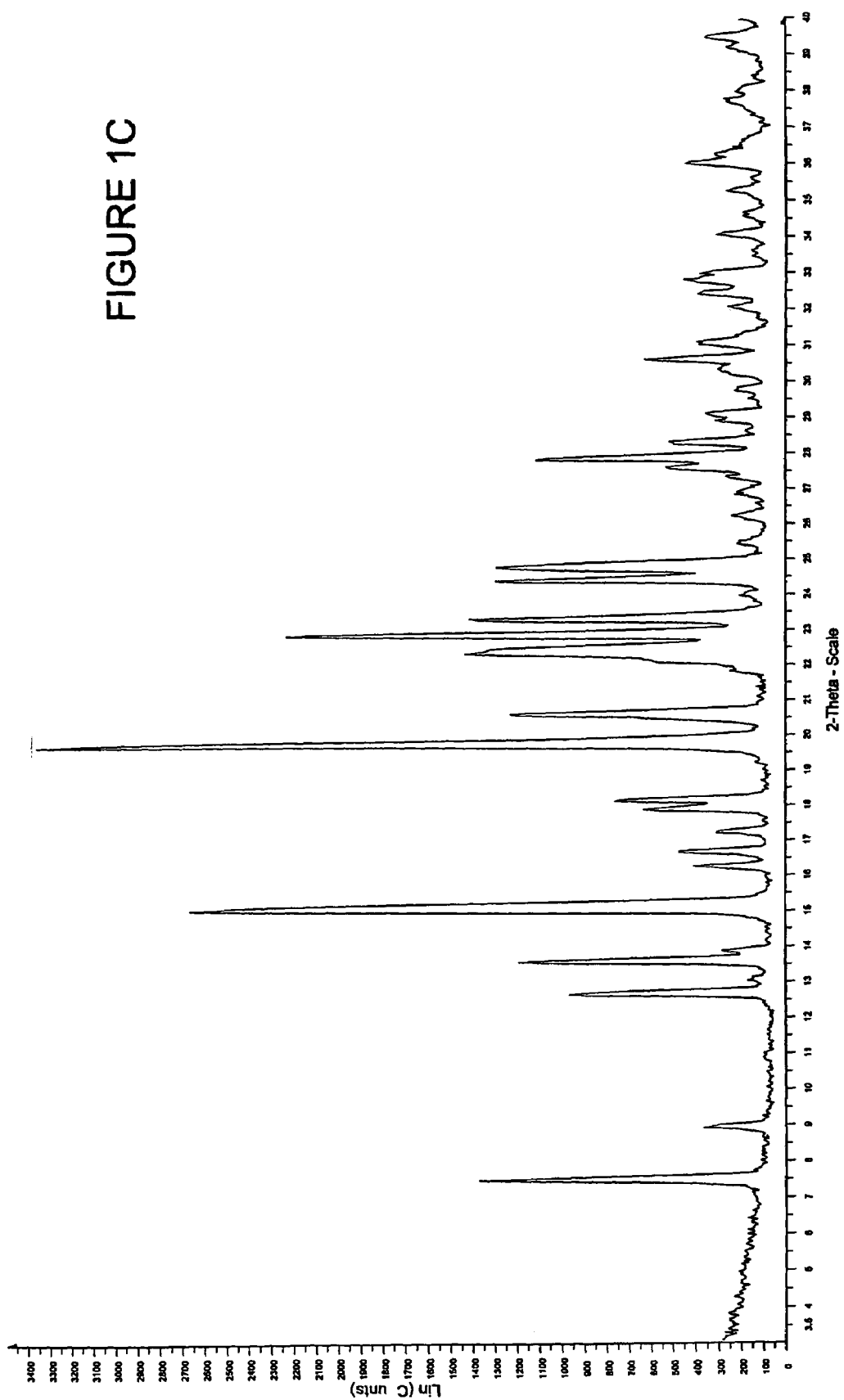
FIG. 1C is the observed powder X-ray diffraction pattern of the benzenesulfonic acid salt of sertraline (y axis is linear counts per second; X in degrees 2 theta).

Sertraline is a selective serotonin reuptake inhibitor useful in the treatment of a number of central nervous system diseases, disorders and conditions. The commercial form of sertraline is its hydrochloride salt sold under the trademark Zoloft®.

Sertraline, including its hydrochloride salt and stable polymorph, and methods of preparing the same, are disclosed in U.S. Pat. Nos. 4,536,518 and 5,248,699. Further methods of preparing sertraline are set forth in U.S. Pat. Nos. 4,777,288; 4,839,104; 4,855,500; 5,463,126; 5,442,116; 5,082,970; 5,466,880; 5,196,607; 5,750,794; 5,288,916; and 6,323,500; as well as in the following published patent applications: International PCT Patent Publication No. WO 99/57089; European Patent Publication Nos. EP 997 535 A1 and EP 1 059 287 A1; and U.S. Patent Publication No. 2001-0044142 A1. All of the foregoing patents and patent publications are hereby incorporated by reference.

The particular pharmaceutically acceptable salts of sertraline of the present invention are only slightly hygroscopic, have high aqueous solubility and high melting points. These characteristics combined with their relative inertness towards common excipients used in pharmaceutical formulations make them highly suitable for pharmaceutical formulation use. In addition, the particular pharmaceutically acceptable salts of the present invention exhibit good solid state stability under accelerated conditions.

Although in general other acid addition salts of sertraline are all crystalline, those salts are in several cases hygroscopic or have unstable crystal forms as to render them poor candidates for pharmaceutical formulation use.

Preparation of the sertraline salts of the invention is carried out ordinarily by dissolving the sertraline free base in a suitable solvent, preferably a $(C_1-C_6)$alkyl ester or ketone, more preferably ethyl acetate or acetone, most preferably ethyl acetate, then adding in the acid to be added to the sertraline free base. The particular acid, i.e., any of p-toluenesulfonic acid, fumaric acid, benzenesulfonic acid, benzoic acid, L-tartaric acid or (−)-camphor-10-sulfonic acid, may be added in solid form to the solution of free base or as a solution in a suitable solvent, preferably in a solvent as listed immediately above, in a preferred 1:1 free base:acid ratio. The mixture is then allowed to stir for several hours to several days. The product salt is then isolated by filtering the reaction mixture, washing the isolated salt in a suitable solvent, and then drying the resultant salt product, preferably in a vacuum oven at a temperature between 25 and 40° C. for approximately 24 to 48 hours. The final product salt is ordinarily harvested in approximately 90 to 100% yield.

Differential Scanning Calorimetry

The solid state thermal behavior of the salts of the invention were investigated by differential scanning calorimetry (DSC). The DSC thermograms were obtained on a Mettler Toledo DSC 821$^e$ (STAR$^e$ System). Generally, samples between 1 and 10 mg were prepared in crimped aluminum pans with a small pinhole. The measurements were run at a heating rate of 5° C. per minute in the range of 30 to 300° C.

Figure 2A:
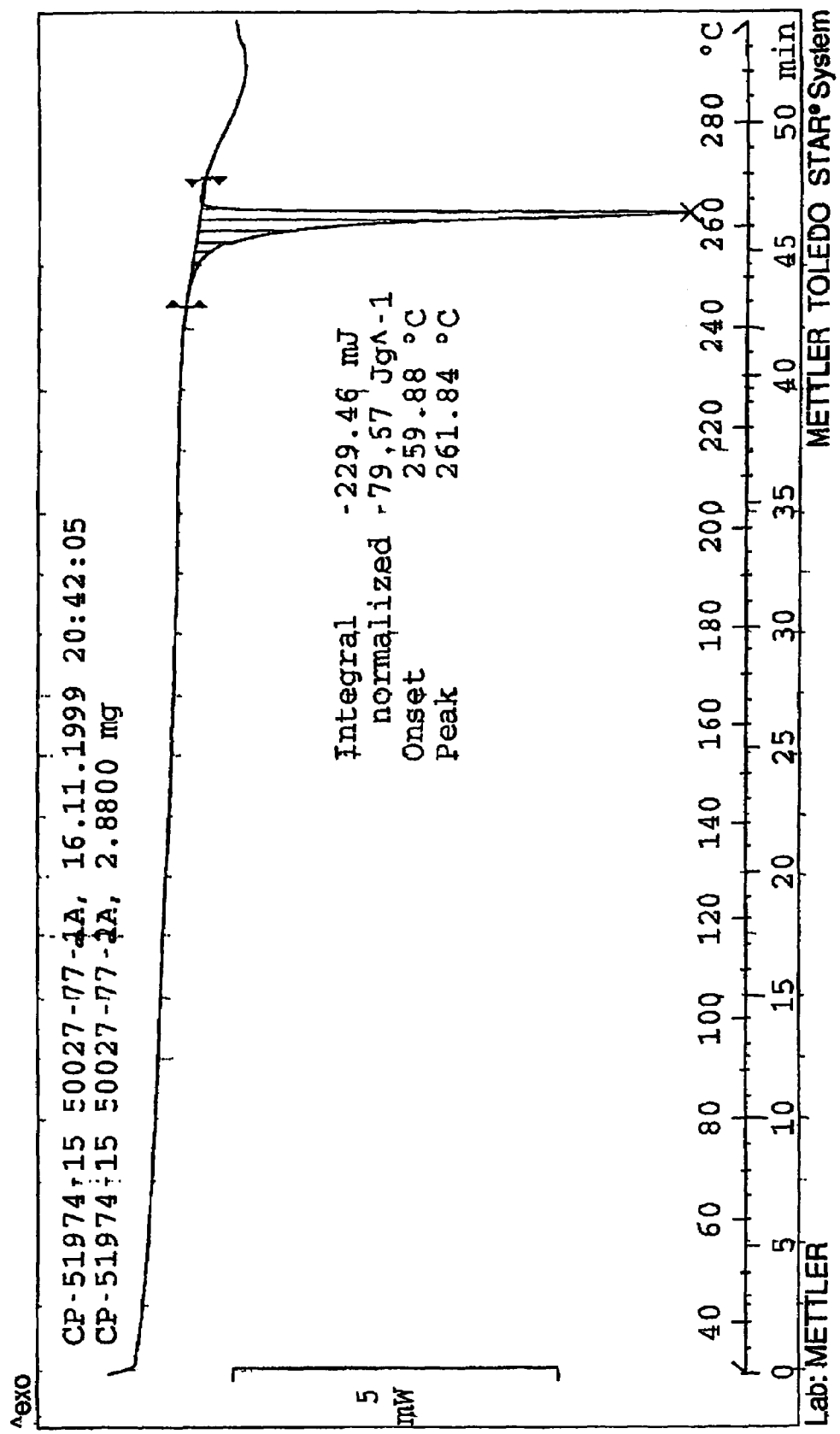
FIG. 2A is the differential scanning calorimetric trace of the p-toluenesulfonic acid salt of sertraline.
Figure 2B:
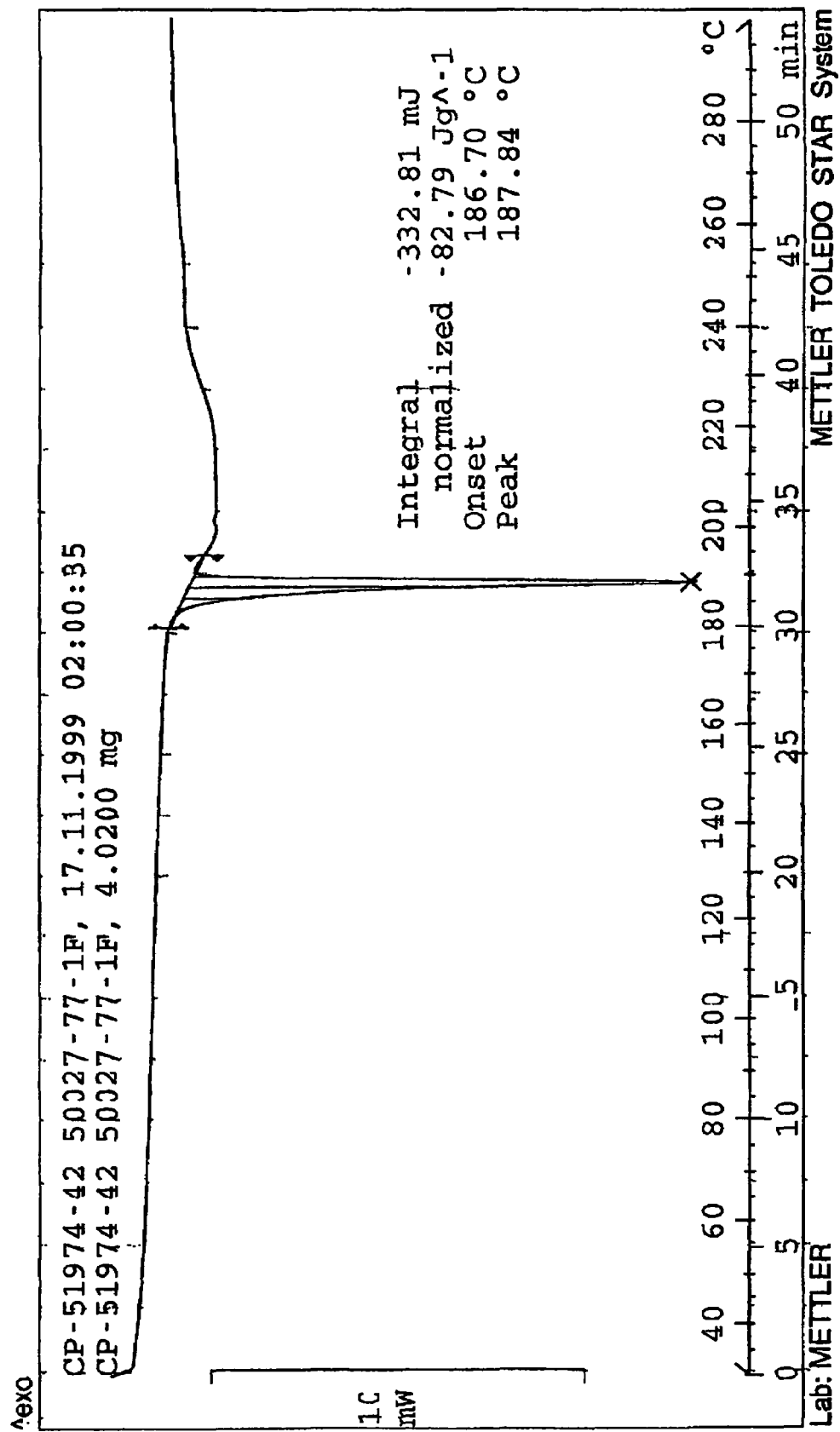
FIG. 2B is the differential scanning calorimetric trace of the fumaric acid salt of sertraline.
Figure 2C:
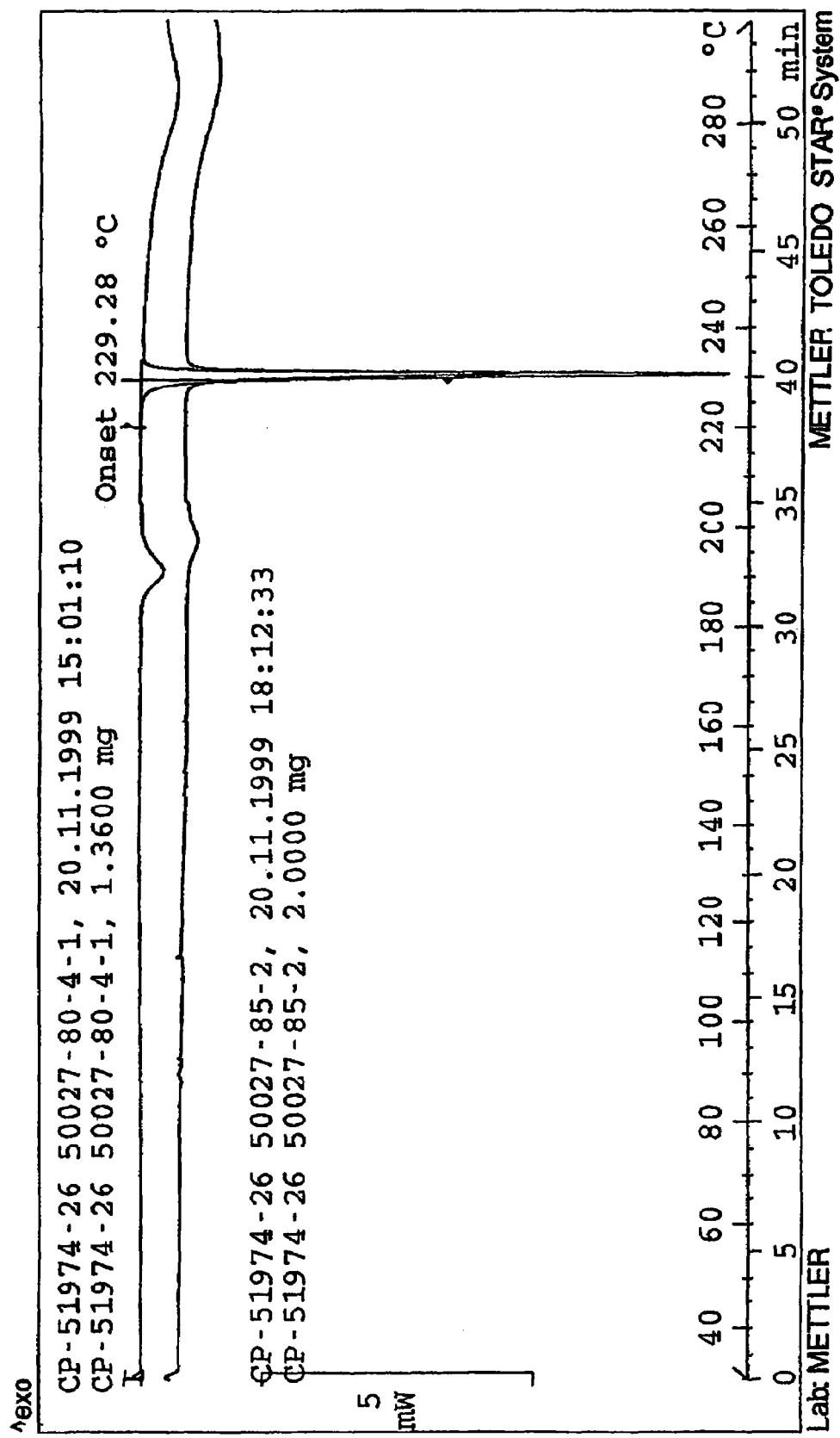
FIG. 2C is the differential scanning calorimetric trace of the benzenesulfonic acid salt of sertraline.
Figure 2D:
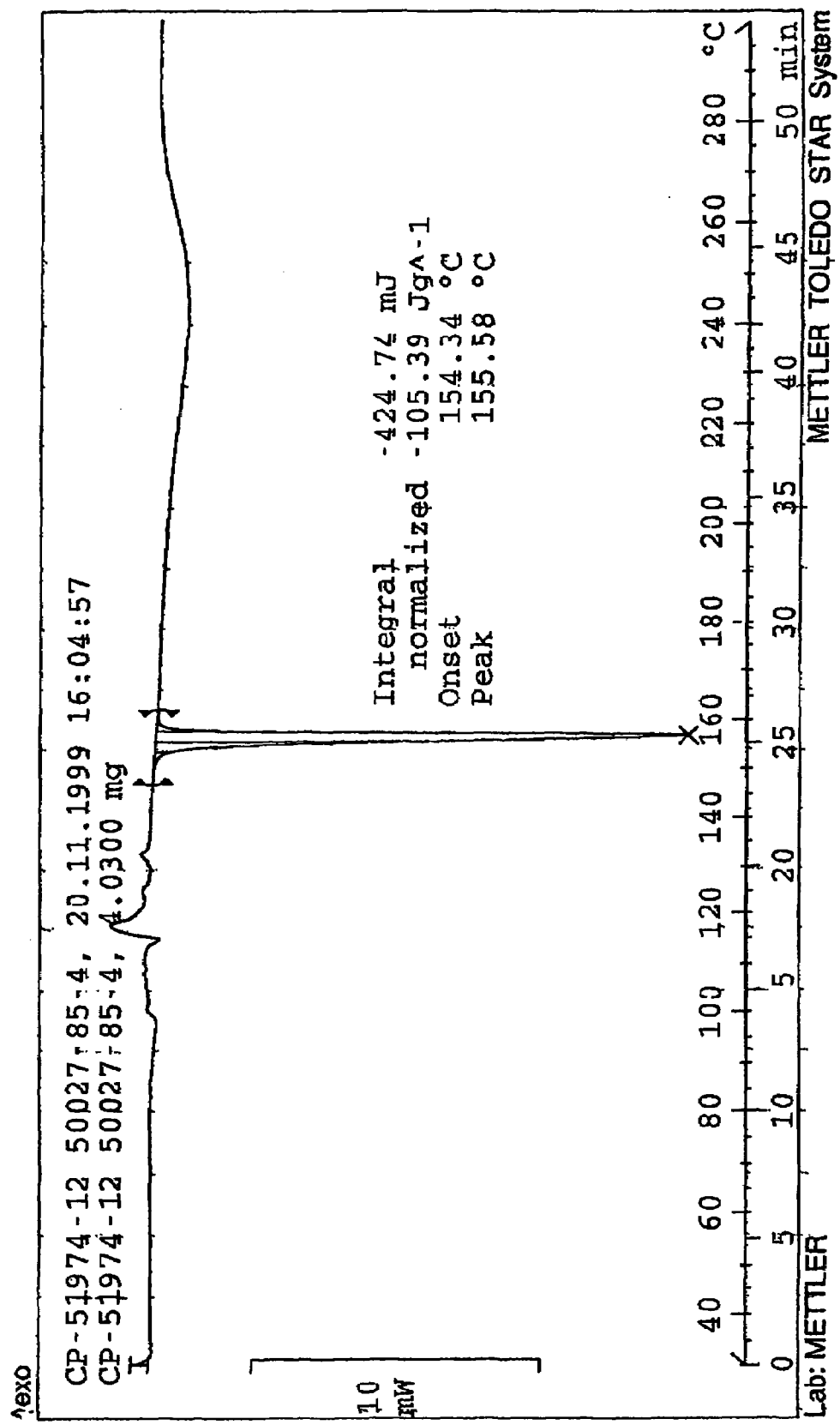
FIG. 2D is the differential scanning calorimetric trace of the benzoic acid salt of sertraline.
Figure 2E:
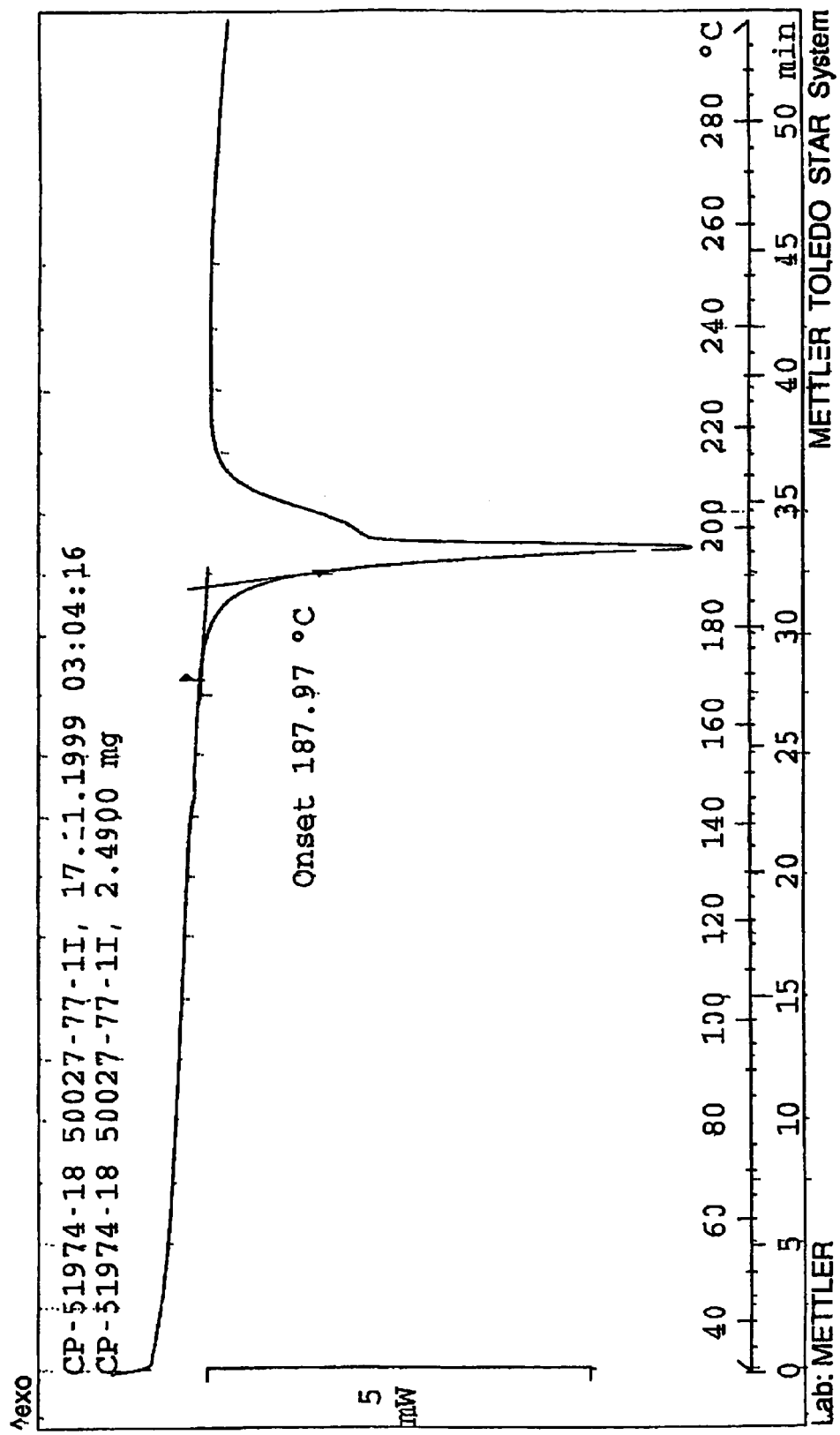
FIG. 2E is the differential scanning calorimetric trace of the L-tartaric acid salt of sertraline.
Figure 2F:
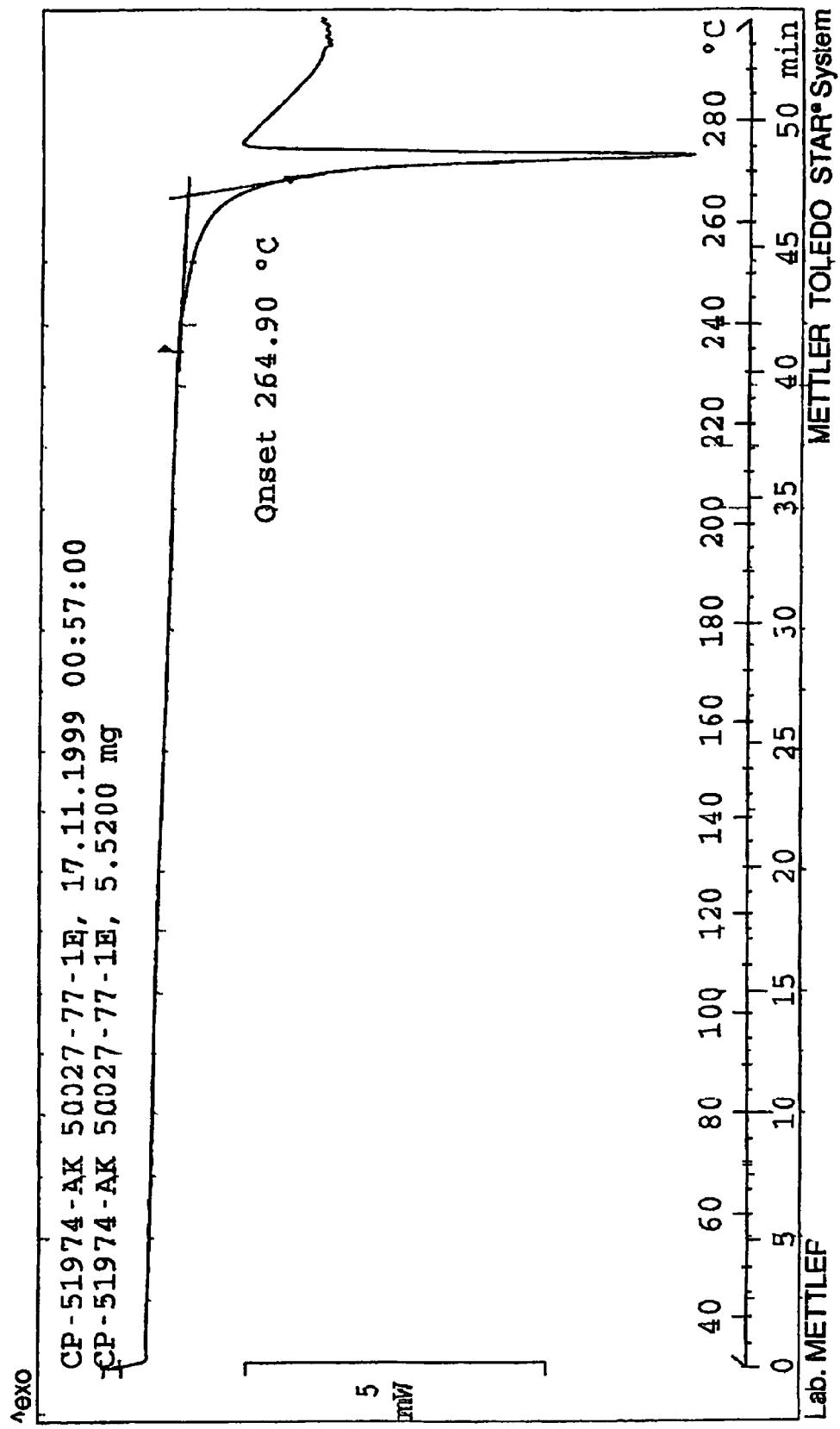
FIG. 2F is the differential scanning calorimetric trace of the (−)-camphor-10-sulfonic acid salt of sertraline.

As seen in FIG. 2A, the p-toluenesulfonic acid salt of sertraline exhibits an onset of melt transition at about 260° C. As seen in FIG. 2B, the fumaric acid salt of sertraline exhibits an onset of melt transition at about 187° C. As seen in FIG. 2C, the benzenesulfonic acid salt of sertraline exhibits an onset of melt transition at about 229° C. As seen in FIG. 2D, the benzoic acid salt of sertraline exhibits an onset of melt transition at about 154° C. As seen in FIG. 2E, the L-tartaric acid salt of sertraline exhibits an onset of melt transition at about 184 ° C. As seen in FIG. 2F, the (−)-camphor-10-sulfonic acid salt of sertraline exhibits an onset of melt transition at about 265 ° C. One of skill in the art will however note that in DSC measurement there is a certain degree of variability in actual measured onset and peak temperatures which occur depending on rate of heating, crystal shape and purity, and other measurement parameters.

Powder X-ray Diffraction Patterns

The power x-ray diffraction patterns for the pharmaceutically acceptable salts of the invention were collected using a Bruker D5000 diffractometer (Bruker AXS, Madison, Wis.) equipped with copper radiation CuK$_\alpha$, fixed slits (1.0, 1.0, 0.6 mm), and a Kevex solid state detector. Data was collected from 3.0 to 40.0 degrees in two theta (2θ) using a step size of 0.04 degrees and a step time of 1.0 seconds.

The x-ray powder diffraction patterns of each of the following salts of sertraline: the p-toluenesulfonic acid salt, the fumaric acid salt, the benzenesulfonic acid salt, the benzoic acid salt, the L-tartaric acid salt and the (−)-camphor-10-sulfonic acid salt, were conducted with a copper anode with wavelength 1 at 1.54056 and wavelength 2 at 1.54439 (relative intensity: 0.500). The range for 2θ was between 3.0 to 40.0 degrees with a step size of 0.04 degrees, a step time of 1.00 second, a smoothing width of 0.300 and a threshold of 1.0.

The diffraction peaks at diffraction angles (2θ) in a measured powder X-ray diffraction analysis for the p-toluenesulfonic acid salt of sertraline are shown in Table I. The relative intensities, however, may change depending on the crystal size and morphology. The actual measured powder diffractogram is displayed in FIG. 1A.

TABLE I

Powder X-ray Diffraction Pattern for the p-Toluenesulfonic Acid Salt of Sertraline with Intensities and Peak Locations of Diffraction Lines.

| Angle 2θ (±0.2) | d-value (Å) (±0.2) | I (rel. %) |
|---|---|---|
| 6.5 | 13.6 | 76.7 |
| 10.0 | 8.9 | 29.2 |
| 12.1 | 7.3 | 29.9 |
| 13.1 | 6.8 | 13.2 |
| 14.2 | 6.2 | 11.6 |
| 16.1 | 5.5 | 60.2 |
| 16.6 | 5.3 | 100.0 |
| 17.5 | 5.1 | 33.3 |
| 18.0 | 4.9 | 23.0 |
| 18.4 | 4.8 | 20.0 |
| 19.6 | 4.5 | 12.8 |
| 20.0 | 4.4 | 37.9 |
| 20.4 | 4.3 | 28.9 |
| 20.8 | 4.3 | 18.6 |
| 21.0 | 4.2 | 15.7 |
| 21.5 | 4.1 | 15.2 |
| 22.2 | 4.0 | 20.0 |
| 22.4 | 4.0 | 24.7 |
| 22.8 | 3.9 | 13.6 |
| 23.7 | 3.8 | 36.6 |
| 24.0 | 3.7 | 35.1 |
| 24.4 | 3.7 | 18.3 |
| 24.9 | 3.6 | 27.8 |
| 25.8 | 3.5 | 48.0 |
| 26.3 | 3.4 | 9.7 |
| 27.1 | 3.3 | 6.8 |
| 27.7 | 3.2 | 8.9 |
| 28.5 | 3.1 | 51.3 |
| 30.0 | 3.0 | 10.5 |
| 31.5 | 2.8 | 14.2 |
| 31.7 | 2.8 | 14.0 |
| 32.5 | 2.8 | 5.4 |
| 33.1 | 2.7 | 6.4 |
| 33.9 | 2.6 | 9.1 |
| 34.7 | 2.6 | 6.8 |
| 35.7 | 2.5 | 5.3 |
| 36.6 | 2.5 | 6.4 |
| 36.9 | 2.4 | 8.4 |
| 38.1 | 2.4 | 5.4 |
| 39.2 | 2.3 | 8.0 |

Table II sets forth the 2θ, d-spacings and relative intensities and peak locations for the powder x-ray diffraction pattern representative for the p-toluenesulfonic acid salt of sertraline. The numbers as listed are computer-generated.

TABLE II

Powder X-ray Diffraction Intensities and Peak Locations Representative of the p-Toluenesulfonic Acid Salt of Sertraline.

| Angle 2θ (±0.2) | d-value (Å) (±0.2) | I (rel. %) |
|---|---|---|
| 6.5 | 13.6 | 76.7 |
| 16.1 | 5.5 | 60.2 |
| 16.6 | 5.3 | 100.0 |
| 20.0 | 4.4 | 37.9 |
| 23.7 | 3.8 | 36.6 |
| 24.0 | 3.7 | 35.1 |
| 25.8 | 3.5 | 48.0 |
| 28.5 | 3.1 | 51.3 |

The diffraction peaks at diffraction angles (2θ) in a measured powder X-ray diffraction analysis for the fumaric acid salt of sertraline are shown in Table III. Again, the relative intensities, however, may change depending on the crystal size and morphology. The actual measured powder diffractogram is displayed in FIG. 1B.

TABLE III

Powder X-ray Diffraction Pattern for the Fumaric Acid Salt of Sertraline with Intensities and Peak Locations of Diffraction Lines.

| Angle 2θ (±0.2) | d-value (Å) (±0.2) | I (rel. %) |
|---|---|---|
| 4.5 | 19.4 | 9.2 |
| 9.1 | 9.7 | 11.8 |
| 10.4 | 8.5 | 4.8 |
| 11.4 | 7.8 | 6.6 |
| 12.5 | 7.1 | 11.0 |
| 13.9 | 6.4 | 54.2 |
| 14.8 | 6.0 | 14.7 |
| 15.5 | 5.7 | 100.0 |
| 16.1 | 5.5 | 25.8 |
| 16.9 | 5.2 | 14.9 |
| 17.3 | 5.1 | 11.4 |
| 18.0 | 4.9 | 11.1 |
| 18.3 | 4.8 | 26.8 |
| 18.6 | 4.8 | 19.0 |
| 19.2 | 4.6 | 41.4 |
| 20.4 | 4.4 | 24.6 |
| 20.8 | 4.3 | 27.9 |
| 21.1 | 4.2 | 25.1 |
| 22.1 | 4.0 | 25.0 |
| 22.4 | 4.0 | 24.3 |
| 23.0 | 3.9 | 78.8 |
| 23.4 | 3.8 | 39.0 |
| 23.9 | 3.7 | 33.3 |
| 25.0 | 3.6 | 24.2 |
| 25.3 | 3.5 | 22.4 |
| 25.9 | 3.4 | 21.4 |
| 27.4 | 3.2 | 40.2 |
| 28.6 | 3.1 | 16.6 |
| 28.8 | 3.1 | 22.1 |
| 29.9 | 3.0 | 14.0 |
| 31.9 | 2.8 | 14.0 |
| 32.4 | 2.8 | 16.9 |
| 33.1 | 2.7 | 12.1 |
| 38.0 | 2.4 | 9.8 |
| 38.3 | 2.3 | 9.3 |

Table IV sets forth the 2θ, d-spacings and relative intensities and peak locations for the powder x-ray diffraction pattern representative for the fumaric acid salt of sertraline. The numbers as listed are computer-generated.

TABLE IV

Powder X-ray Diffraction Intensities and Peak Locations Representative of the Fumaric Acid Salt of Sertraline.

| Angle 2θ (±0.2) | d-value (Å) (±0.2) | I (rel. %) |
|---|---|---|
| 13.9 | 6.4 | 54.2 |
| 15.5 | 5.7 | 100.0 |
| 18.3 | 4.8 | 26.8 |
| 19.1 | 4.6 | 41.4 |
| 20.8 | 4.3 | 27.9 |
| 23.0 | 3.9 | 78.8 |
| 23.4 | 3.8 | 39.0 |
| 27.4 | 3.2 | 40.2 |

The diffraction peaks at diffraction angles (2θ) in a measured powder X-ray diffraction analysis for the benzenesulfonic acid salt of sertraline are shown in Table V. Again, the relative intensities, however, may change depending on the crystal size and morphology. The actual measured powder diffractogram is displayed in FIG. 1C.

TABLE V

Powder X-ray Diffraction Pattern for the Benzenesulfonic Acid Salt of Sertraline with Intensities and Peak Locations of Diffraction Lines.

| Angle 2θ (±0.2) | d-value (Å) (±0.2) | I (rel. %) |
|---|---|---|
| 7.5 | 11.9 | 40.6 |
| 8.9 | 10.0 | 10.5 |
| 12.7 | 7.0 | 28.5 |
| 13.0 | 6.8 | 4.7 |
| 13.6 | 6.5 | 35.1 |
| 13.8 | 6.4 | 6.3 |
| 15.1 | 5.9 | 79.3 |
| 16.2 | 5.5 | 11.8 |
| 16.7 | 5.3 | 13.6 |
| 17.2 | 5.2 | 8.7 |
| 17.9 | 5.0 | 18.5 |
| 18.2 | 4.9 | 22.3 |
| 19.8 | 4.5 | 100.0 |
| 20.6 | 4.3 | 36.3 |
| 22.4 | 4.0 | 42.4 |
| 22.9 | 3.9 | 66.4 |
| 23.4 | 3.8 | 41.9 |
| 24.0 | 3.7 | 5.8 |
| 24.4 | 3.6 | 38.3 |
| 24.8 | 3.6 | 38.2 |
| 25.5 | 3.5 | 6.2 |
| 26.2 | 3.4 | 6.7 |
| 26.9 | 3.3 | 6.3 |
| 27.4 | 3.3 | 5.8 |
| 27.6 | 3.2 | 15.4 |
| 27.9 | 3.2 | 32.9 |
| 28.3 | 3.1 | 14.9 |
| 28.9 | 3.1 | 8.0 |
| 29.1 | 3.1 | 10.1 |
| 29.8 | 3.0 | 6.4 |
| 30.3 | 2.9 | 8.6 |
| 30.6 | 2.9 | 18.3 |
| 31.1 | 2.9 | 11.3 |
| 32.1 | 2.8 | 7.3 |
| 32.5 | 2.8 | 11.2 |
| 32.8 | 2.7 | 13.1 |
| 33.0 | 2.7 | 8.7 |
| 33.6 | 2.7 | 4.2 |
| 34.1 | 2.6 | 8.8 |
| 34.6 | 2.6 | 5.4 |
| 35.3 | 2.5 | 7.4 |
| 36.1 | 2.5 | 12.8 |
| 36.3 | 2.5 | 8.2 |
| 36.6 | 2.5 | 5.5 |
| 37.7 | 2.4 | 7.5 |
| 38.1 | 2.4 | 5.9 |
| 38.4 | 2.3 | 4.1 |
| 39.2 | 2.3 | 7.4 |
| 39.5 | 2.3 | 10.1 |

Table VI sets forth the 2θ, d-spacings and relative intensities and peak locations for the powder x-ray diffraction pattern representative for the benzenesulfonic acid salt of sertraline. The numbers as listed are computer-generated.

TABLE VI

Powder X-ray Diffraction Intensities and Peak Locations Representative of the Benzenesulfonic Acid Salt of Sertraline.

| Angle 2θ (±0.2) | d-value (Å) (±0.2) | I (rel. %) |
|---|---|---|
| 7.5 | 11.9 | 40.6 |
| 15.1 | 5.9 | 79.3 |
| 22.4 | 4.0 | 42.4 |
| 22.9 | 3.9 | 66.4 |
| 23.4 | 3.8 | 41.9 |

TABLE VI-continued

Powder X-ray Diffraction Intensities and Peak Locations Representative of the Benzenesulfonic Acid Salt of Sertraline.

| Angle 2θ (±0.2) | d-value (Å) (±0.2) | I (rel. %) |
|---|---|---|
| 24.4 | 3.6 | 38.3 |
| 24.8 | 3.6 | 38.2 |
| 27.9 | 3.2 | 32.9 |

The diffraction peaks at diffraction angles (2θ) in a measured powder X-ray diffraction analysis for the benzoic acid salt of sertraline are shown in Table VII. Again, the relative intensities, however, may change depending on the crystal size and morphology. The actual measured powder diffractogram is displayed in FIG. 1D.

TABLE VII

Powder X-ray Diffraction Pattern for the Benzoic Acid Salt of Sertraline with Intensities and Peak Locations of Diffraction Lines.

| Angle 2θ (±0.2) | d-value (Å) (±0.2) | I (rel. %) |
|---|---|---|
| 8.0 | 11.0 | 6.7 |
| 10.1 | 8.8 | 4.7 |
| 11.7 | 7.5 | 12.0 |
| 13.2 | 6.7 | 23.4 |
| 13.6 | 6.5 | 16.2 |
| 14.9 | 5.9 | 47.3 |
| 16.1 | 5.5 | 100.0 |
| 16.7 | 5.3 | 12.7 |
| 18.0 | 4.9 | 46.0 |
| 18.5 | 4.8 | 33.7 |
| 19.3 | 4.6 | 32.6 |
| 20.3 | 4.4 | 9.0 |
| 21.1 | 4.2 | 28.2 |
| 21.7 | 4.1 | 17.9 |
| 22.4 | 4.0 | 13.4 |
| 22.7 | 3.9 | 13.9 |
| 23.2 | 3.8 | 31.8 |
| 23.6 | 3.8 | 40.0 |
| 24.2 | 3.7 | 11.3 |
| 25.0 | 3.6 | 39.5 |
| 25.2 | 3.5 | 37.4 |
| 25.7 | 3.5 | 10.7 |
| 26.1 | 3.4 | 20.9 |
| 26.6 | 3.3 | 50.0 |
| 27.2 | 3.3 | 22.9 |
| 28.0 | 3.2 | 6.9 |
| 28.5 | 3.1 | 7.1 |
| 29.0 | 3.1 | 8.7 |
| 30.1 | 3.0 | 7.6 |
| 30.5 | 2.9 | 19.3 |
| 31.8 | 2.8 | 15.3 |
| 32.4 | 2.8 | 15.4 |
| 34.2 | 2.6 | 13.6 |
| 34.5 | 2.6 | 10.3 |
| 36.4 | 2.5 | 6.9 |
| 37.0 | 2.4 | 7.0 |
| 37.4 | 2.4 | 7.7 |
| 38.0 | 2.4 | 5.9 |
| 39.6 | 2.3 | 5.5 |

TABLE VIII

Powder X-ray Diffraction Intensities and Peak Locations Representative of the Benzoic Acid Salt of Sertraline

| Angle 2θ (±0.2) | d-value (Å) (±0.2) | I (rel. %) |
|---|---|---|
| 14.9 | 5.9 | 47.3 |
| 16.1 | 5.5 | 100.0 |
| 18.0 | 4.9 | 46.0 |
| 18.5 | 4.8 | 33.7 |
| 19.3 | 4.6 | 32.6 |
| 23.6 | 3.8 | 40.0 |
| 25.0 | 3.6 | 39.5 |
| 25.2 | 3.5 | 37.4 |

The diffraction peaks at diffraction angles (2θ) in a measured powder X-ray diffraction analysis for the L-tartaric acid salt of sertraline are shown in Table IX. Again, the relative intensities, however, may change depending on the crystal size and morphology. The actual measured powder diffractogram is displayed in FIG. 1B.

TABLE IX

Powder X-ray Diffraction Pattern for the L-Tartaric Acid Salt of Sertraline with Intensities and Peak Locations of Diffraction Lines.

| Angle 2θ (±0.2) | d-value (Å) (±0.2) | I (rel. %) |
|---|---|---|
| 4.1 | 21.7 | 20.0 |
| 8.2 | 10.8 | 17.8 |
| 10.0 | 8.8 | 9.5 |
| 10.4 | 8.5 | 3.5 |
| 11.3 | 7.8 | 10.8 |
| 12.2 | 7.2 | 24.0 |
| 13.7 | 6.5 | 55.0 |
| 15.0 | 5.9 | 100.0 |
| 16.4 | 5.4 | 26.9 |
| 16.7 | 5.3 | 45.7 |
| 17.1 | 5.2 | 11.4 |
| 17.4 | 5.1 | 14.7 |
| 18.4 | 4.8 | 31.2 |
| 19.0 | 4.7 | 8.4 |
| 20.2 | 4.4 | 14.7 |
| 20.5 | 4.3 | 68.1 |
| 20.9 | 4.2 | 10.0 |
| 22.1 | 4.0 | 38.5 |
| 22.9 | 3.9 | 54.9 |
| 23.9 | 3.7 | 22.1 |
| 24.5 | 3.6 | 42.8 |
| 25.6 | 3.5 | 5.8 |
| 26.2 | 3.4 | 29.0 |
| 26.6 | 3.4 | 23.1 |
| 27.1 | 3.3 | 6.3 |
| 27.5 | 3.2 | 11.7 |
| 28.9 | 3.1 | 9.2 |
| 29.9 | 3.0 | 15.8 |
| 30.5 | 2.9 | 14.4 |
| 31.4 | 2.8 | 14.2 |
| 32.0 | 2.8 | 15.7 |
| 32.4 | 2.8 | 11.4 |
| 32.9 | 2.7 | 14.6 |
| 33.5 | 2.7 | 9.2 |
| 34.7 | 2.6 | 9.0 |
| 35.8 | 2.5 | 5.0 |
| 36.7 | 2.4 | 7.0 |
| 37.3 | 2.4 | 6.1 |
| 37.9 | 2.4 | 10.2 |
| 39.0 | 2.3 | 8.4 |

Table VIII sets forth the 2θ, d-spacings and relative intensities and peak locations for the powder x-ray diffraction pattern representative for the benzoic acid salt of sertraline. The numbers as listed are computer-generated.

Table X sets forth the 2θ, d-spacings and relative intensities and peak locations for the powder x-ray diffraction pattern representative for the L-tartaric acid salt of sertraline. The numbers as listed are computer-generated.

TABLE X

Powder X-ray Diffraction Intensities and Peak Locations
Representative of the L-Tartaric Acid Salt of Sertraline.

| Angle 2θ (±0.2) | d-value (Å) (±0.2) | I (rel. %) |
| --- | --- | --- |
| 13.7 | 6.5 | 55.0 |
| 15.0 | 5.9 | 100.0 |
| 16.7 | 5.3 | 45.7 |
| 18.4 | 4.8 | 31.2 |
| 20.5 | 4.3 | 68.1 |
| 22.1 | 4.0 | 38.5 |
| 22.9 | 3.9 | 54.9 |
| 24.5 | 3.6 | 42.8 |

The diffraction peaks at diffraction angles (2θ) in a measured powder X-ray diffraction analysis for the (−)-camphor-10-sulfonic acid salt of sertraline are shown in Table XI. Again, the relative intensities, however, may change depending on the crystal size and morphology. The actual measured powder diffractogram is displayed in FIG. 1B.

TABLE XI

Powder X-ray Diffraction Pattern for the (−)-Camphor-10-sulfonic acid Salt of Sertraline with Intensities and Peak Locations of Diffraction Lines.

| Angle 2θ (±0.2) | d-value (Å) (±0.2) | I (rel. %) |
| --- | --- | --- |
| 5.6 | 15.8 | 100.0 |
| 7.2 | 12.2 | 9.8 |
| 9.4 | 9.4 | 11.1 |
| 11.2 | 7.9 | 11.2 |
| 12.3 | 7.2 | 5.0 |
| 13.1 | 6.8 | 53.2 |
| 13.4 | 6.6 | 8.2 |
| 13.7 | 6.4 | 13.6 |
| 14.6 | 6.1 | 48.3 |
| 15.1 | 5.9 | 23.9 |
| 15.9 | 5.6 | 92.4 |
| 16.9 | 5.2 | 14.3 |
| 17.2 | 5.1 | 19.3 |
| 17.6 | 5.0 | 23.4 |
| 17.7 | 5.0 | 19.0 |
| 18.2 | 5.9 | 28.9 |
| 19.2 | 4.6 | 14.2 |
| 19.5 | 4.5 | 16.8 |
| 19.9 | 4.5 | 39.0 |
| 20.6 | 4.3 | 16.8 |
| 20.8 | 4.3 | 10.4 |
| 21.4 | 4.1 | 21.1 |
| 21.7 | 4.1 | 45.8 |
| 22.1 | 4.0 | 17.9 |
| 22.6 | 3.9 | 29.8 |
| 23.0 | 3.9 | 28.5 |
| 23.5 | 3.8 | 20.3 |
| 24.0 | 3.7 | 17.3 |
| 24.4 | 3.6 | 11.4 |
| 24.8 | 3.6 | 20.5 |
| 26.3 | 3.4 | 10.7 |
| 26.8 | 3.3 | 12.0 |
| 27.1 | 3.3 | 10.7 |
| 28.3 | 3.1 | 12.1 |
| 29.0 | 3.1 | 7.9 |
| 30.4 | 2.9 | 9.5 |
| 30.8 | 2.9 | 9.4 |
| 31.8 | 2.8 | 7.7 |
| 32.2 | 2.8 | 7.4 |
| 32.7 | 2.7 | 7.4 |
| 33.8 | 2.6 | 8.1 |
| 34.2 | 2.6 | 9.4 |
| 35.4 | 2.5 | 6.8 |
| 36.0 | 2.5 | 6.5 |
| 38.7 | 2.3 | 7.1 |

TABLE XI-continued

Powder X-ray Diffraction Pattern for the (−)-Camphor-10-sulfonic acid Salt of Sertraline with Intensities and Peak Locations of Diffraction Lines.

| Angle 2θ (±0.2) | d-value (Å) (±0.2) | I (rel. %) |
| --- | --- | --- |
| 39.6 | 2.3 | 7.1 |
| 39.8 | 2.3 | 6.7 |

Table XII sets forth the 2θ, d-spacings and relative intensities and peak locations for the powder x-ray diffraction pattern representative for the (−)-camphor-10-sulfonic acid salt of sertraline. The numbers as listed are computer-generated.

TABLE IV

Powder X-ray Diffraction Intensities and Peak Locations Representative of the (−)-Camphor-10-sulfonic Acid Salt of Sertraline.

| Angle 2θ (±0.2) | d-value (Å) (±0.2) | I (rel. %) |
| --- | --- | --- |
| 5.6 | 15.8 | 100.0 |
| 13.1 | 6.8 | 53.2 |
| 14.6 | 6.1 | 48.3 |
| 15.8 | 5.6 | 92.4 |
| 18.2 | 4.9 | 28.9 |
| 19.9 | 4.5 | 39.0 |
| 21.7 | 4.1 | 45.8 |
| 22.6 | 3.9 | 29.8 |

The pharmaceutically acceptable sertraline salts of the invention, including the p-toluenesulfonic acid salt, the fumaric acid salt, the benzenesulfonic acid salt, the benzoic acid salt, the L-tartaric acid salt and the (−)-camphor-10-sulfonic acid salt (hereafter "the active salts"), can be administered via either the oral, transdermal (e., through the use of a patch), intranasal, sublingual, rectal, parenteral or topical routes. Transdermal and oral administration are preferred. The active salt is, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active salts of the invention can be administered alone or in combination with pharmaceutically acceptable carriers or diluents by any of the several routes previously indicated. More particularly, the active salt can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active salt is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active salt may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active salt in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active salts topically and this can be done by way of creams, a patch, jellies, gels, pastes, ointments and the like, in accordance with standard pharmaceutical practice.

The following examples illustrate the methods and compounds of the present invention. It will be understood, however, that the invention is not limited to the specific Examples.

EXAMPLE 1

P-Toluenesulfonic Acid Salt of Sertraline

A 50 ml flask was charged with the free base sertraline (300 mg; 0.98 mmol) and ethyl acetate (5 ml). The mixture was filtered to remove any specks and fibers present. To the clarified solution was added tosic acid monohydrate (186 mg., 0.98 mmol, 1.0 equiv.) dissolved in ethyl acetate (5 ml) and stirred at room temperature overnight. The product was isolated by filtration, washed with cold ethyl acetate and dried at 20 to 30° C. under vacuum for about 24 hours. The identity of the title compound was verified by powder x-ray diffraction. Yield: 463 mg (0.96 mmol; 99%) Elem. Anal. Obs'd: C 60.33%, H 5.32%, N 3.02%, S 6.94%; Calc'd C 60.25%, H 5.27%, N 2.93%, S 6.70%.

EXAMPLE 2

Fumaric Acid Salt of Sertraline

A 50 ml flask was charged with the free base sertraline (300 mg; 0.98 mmol) and ethyl acetate (5 ml). The mixture was filtered to remove any specks and fibers present. To the clarified solution was added fumaric acid (114 mg., 0.98 mmol, 1.0 equiv.) dissolved in ethyl acetate (5 ml). The mixture was stirred over 48 hours and the final slurry of white precipitate was isolated by filtration, washed with ethyl acetate and dried at 45° C. under vacuum for about 24 hours. Yield 397 mg (0.94 mmol; 96%). The identity of the title compound was verified by powder x-ray diffraction. Elem. Anal. Obs'd: C 59.77%, H 5.16%, N 3.34%; Calc'd C 59.73%, H 5.01%, N 3.32%.

EXAMPLE 3

Benzenesulfonic Acid Salt of Sertraline

A 50 ml flask was charged with the free base sertraline (300 g; 0.98 mmol) and ethyl acetate (5 ml). The mixture was filtered to remove any specks and fibers present. To the clarified solution was added benzenesulfonic acid (155 g., 0.98 mmol, 1.0 equiv.) dissolved in ethyl acetate. The mixture was stirred at overnight at room temperature allowing crystallization to occur. The product was isolated by filtration, washed with ethyl acetate and dried at 20 to 30° C. under vacuum for about 24 hours. The identity of the title compound was verified by powder x-ray diffraction. Yield: 399 mg (0.86 mmol; 88%). Elem. Anal. Obs'd: C 59.56%, H 4.85%, N 3.01%, S 7.26%; Calc'd C 59.49%, H 4.99%, N 3.02%, S 6.90%.

EXAMPLE 4

Benzoic Acid Salt of Sertraline

A 50 ml flask was charged with the free base sertraline (153.3 mg; 0.50 mmol) and ethyl acetate (5 ml). The mixture was filtered to remove any specks and fibers present. To the clarified solution was added with a benzoic acid (62 mg., 0.51 mmol, 1.0 equiv.) dissolved in acetone (5 ml). The mixture was stirred at room temperature for 48 hours. The product was isolated by filtration, washed with acetone and dried at 20 to 30° C. under vacuum for about 24 hours. The identity of the title compound was verified by powder x-ray diffraction. Elem. Anal. Obs'd: C 67.33%, H 5.56%, N 3.21%; Calc'd C 67.30%, H 5.41%, N 3.27%.

EXAMPLE 5

L-Tartaric Acid Salt of Sertraline

A 50 ml flask was charged with the free base sertraline (300 mg; 0.98 mmol) and ethyl acetate (5 ml). The mixture was filtered to remove any specks and fibers present. To the clarified solution was added L-tartaric acid (147 mg., 0.98 mmol, 1.0 equiv.) dissolved in ethyl acetate (5 ml). The mixture was stirred at overnight and the product was isolated by filtration, washed with ethyl acetate and dried at 20 to 30° C. under vacuum for about 24 hours. The identity of the title compound was verified by powder x-ray diffraction. Yield: 439 mg (0.96 mmol; 98%) Elem. Anal. Obs'd: C 55.23%, H 5.07%, N 3.06%; Calc'd C 55.27%, H 5.08%, N 3.07%.

EXAMPLE 6

(−)-Camphor-10-sulfonic Acid Salt of Sertraline

A 50 ml flask was charged with the free base sertraline (300 mg; 0.98 mmol) and ethyl acetate (5 ml). The mixture was filtered to remove any specks and fibers present. To the clarified solution was added a solution of (−)-camphor-10-sulfonic acid (228 mg., 0.98 mmol, 1.0 equiv.) dissolved in ethyl acetate (5 ml) over heat. The resultant crystal slurry was allowed cooled to room temperature and stirred for about 4 hours. The product was isolated by filtration, washed with ethyl acetate and dried at 45° C. under vacuum for about 48 hours. The identity of the title compound was verified by powder x-ray diffraction. Yield: 508 mg (0.94 mmol; 96%) Elem. Anal. Obs'd: C 60.28%, H 6.22%, N 2.61%, S 6.19%; Theor. C 60.22%, H 6.18%, N 2.60%, S 5.95%.

What is claimed is:

1. An acid addition salt of sertraline:

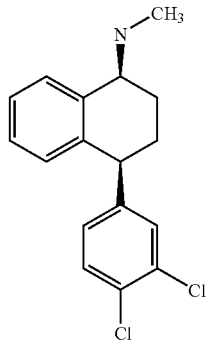

wherein said salt is selected from the group consisting of the p-toluenesulfonic acid salt, the fumaric acid salt, the benzenesulfonic acid salt, the benzoic acid salt, and the L-tartaric acid salt.

2. The salt according to claim 1 wherein the salt is the p-toluenesulfonic acid salt.

3. The salt according to claim 2 having an x-ray diffraction pattern characterized by an x-ray diffraction pattern peak expressed in terms of an angle 2θ of 16.6 degrees ±0.2 degrees as measured with copper radiation.

4. The salt according to claim 2 having an x-ray diffraction pattern characterized by the following principal x-ray diffraction pattern peaks expressed in terms of an angle of 2θ degrees and d-spacings in E, within the margins of error indicated, as measured with copper radiation:

| Angle 2θ (±0.2) | d-value (Å) (±0.2) |
|---|---|
| 6.5 | 13.6 |
| 16.1 | 5.5 |
| 16.6 | 5.3 |
| 20.0 | 4.4 |
| 23.7 | 3.8 |
| 24.0 | 3.7 |
| 25.8 | 3.5 |
| 28.5 | 3.1. |

5. The salt according to claim 2 characterized in having an onset of melting transition at about 260° C.

6. The salt according to claim 1 wherein the salt is the fumaric acid salt.

7. The salt according to claim 6 having an x-ray diffraction pattern characterized by an x-ray diffraction pattern peak expressed in terms of an angle 2θ of 15.5 degrees ±0.2 degrees as measured with copper radiation.

8. The salt according to claim 6 having an x-ray diffraction pattern characterized by the following principal x-ray diffraction pattern peaks expressed in terms of an angle of 2θ degrees and d-spacings in E, within the margins of error indicated, as measured with copper radiation:

| Angle 2θ (±0.2) | d-value (Å) (±0.2) |
|---|---|
| 13.9 | 6.4 |
| 15.5 | 5.7 |
| 18.3 | 4.8 |
| 19.1 | 4.6 |
| 20.8 | 4.3 |
| 23.0 | 3.9 |
| 23.4 | 3.8 |
| 27.4 | 3.2. |

9. The salt according to claim 6 characterized in having an onset of melting transition at about 187° C.

10. The salt according to claim 1 wherein the salt is the benzenesulfonic acid salt.

11. The salt according to claim 10 characterized in having a solid-solid transition at about 185° C. and an onset of melting transition at about 230° C.

12. The salt according to claim 1 wherein the salt is the benzoic acid salt.

13. The salt according to claim 12 having an x-ray diffraction pattern characterized by an x-ray diffraction pattern peak expressed in terms of an angle 2θ of 16.1 degrees ±0.2 degrees as measured with copper radiation.

14. The salt according to claim 12 having an x-ray diffraction pattern characterized by the following principal x-ray diffraction pattern peaks expressed in terms of an angle of 2θ degrees and d-spacings in E, within the margins of error indicated, as measured with copper radiation:

| Angle 2θ (±0.2) | d-value (Å) (±0.2) |
|---|---|
| 14.9 | 5.9 |
| 16.1 | 5.5 |
| 18.0 | 4.9 |
| 18.5 | 4.8 |
| 19.3 | 4.6 |
| 23.6 | 4.4 |
| 25.0 | 3.6 |
| 25.2 | 3.5. |

15. The salt according to claim 12 characterized in having an onset of melting transition at about 154° C.

16. The salt according to claim 1 wherein the salt is the L-tartaric acid salt.

17. The salt according to claim 16 having an x-ray diffraction pattern characterized by an x-ray diffraction pattern peak expressed in terms of an angle 2θ of 15.0 degrees ±0.2 degrees as measured with copper radiation.

18. The salt according to claim 16 having an x-ray diffraction pattern characterized by the following principal x-ray diffraction pattern peaks expressed in terms of an angle of 2° degrees and d-spacings in E, within the margins of error indicated, as measured with copper radiation:

| Angle 2θ (±0.2) | d-value (Å) (±0.2) |
|---|---|
| 13.7 | 6.5 |
| 15.0 | 5.9 |
| 16.7 | 5.3 |
| 18.4 | 4.8 |
| 20.5 | 4.3 |
| 22.1 | 4.0 |
| 22.9 | 3.9 |
| 24.5 | 3.6. |

19. A pharmaceutical composition comprising a salt according to claim 1 and a pharmaceutically acceptable carrier or excipient.

20. A method of treating in a mammal a disease, disorder or condition selected from the group consisting of aggression disorders; anxiety disorders, panic attack, agoraphobia, panic disorder with or without agoraphobia, agoraphobia without history of panic disorder, specific phobia, social phobia, obsessive-compulsive disorder, post-traumatic stress disorder and acute stress disorder; cognitive disorders selected from the group consisting of amnestic disorders, amnestic disorders due to a general medical condition, substance-induced persisting amnestic disorder and amnestic disorders not otherwise specified, deliriums, deliriums due to a general medical condition, substance-induced delirium and delirium not otherwise specified, dementias, dementia of the Alzheimer's type, vascular dementia, dementia due to a general medical condition; AIDS-, Parkinson's-, head trauma-, and Huntington's-induced dementias; substance-induced persisting dementia, dementia due to multiple etiologies; depression disorders; emesis; epilepsy; food-related behavioral disorders, anorexia nervosa, bulimia; headache disorders, migraine; cluster and vascular headaches; learning disorders, attention deficit disorder, attention deficit/hyperactivity disorder; obesity; ocular disorders; platelet aggregation disorders; psychotic conditions, schizophrenia, paranoid-type schizophrenia, disorganized-type schizophrenia, catatonic-type schizophrenia, undifferentiated-type schizophrenia, residual-type schizophrenia, schizophreniform disorder, schizoaffective disorder, delusional disorder, brief psychotic disorder, shared psychotic disorder, psychotic disorders due to a general medical condition; sleep disorders, primary sleep disorders, parasomnias, dyssomnias, sleep disorders related to another mood and anxiety disorders, sleep disorders due to a general medical condition; sexual behavior disorders; substance-abuse disorders, alcohol-related disorders; alcohol-use disorders selected from dependence and abuse disorders; alcohol-induced disorders selected from intoxication, withdrawal, intoxication delirium, withdrawal delirium, persisting dementia, persisting amnestic, mood, anxiety, sexual dysfunction, and sleep disorders; amphetamine-related disorders; amphetamine-use disorders selected from dependence and abuse disorders; amphetamine-induced disorders selected from intoxication, withdrawal, intoxication delirium, psychotic, mood, anxiety, sexual dysfunction and sleep disorders; caffeine-related disorders selected from as intoxication, induced-anxiety disorder, induced-sleep disorder; cannabis-related disorders, cannabis-use disorders selected from abuse and dependence disorders; cannabis-induced disorders selected from intoxication, intoxication delirium, psychotic disorder, and anxiety disorders; cocaine-related disorders; cocaine-use disorders selected from dependence and abuse disorders; cocaine-induced disorders selected from intoxication, withdrawal, intoxication delirium, psychotic, mood, anxiety, sexual dysfunction, sleep disorder; hallucinogen-related disorders, hallucinogen-use disorders selected from dependence and abuse disorders; hallucinogen-induced disorders selected from intoxication, persisting perception, intoxication delirium, psychotic, mood, and anxiety disorder; inhalant-related disorders, inhalant-use disorders selected from dependence and abuse disorders; inhalant-induced disorders selected from intoxication, intoxication delirium, persisting dementia, psychotic, mood, and anxiety disorder; nicotine-related disorders selected from dependence and withdrawal; opioid-related disorders, opioid-use disorders selected form dependence and abuse disorders; opioid-induced disorders selected from intoxication, withdrawal, intoxication delirium, psychotic, mood, sexual dysfunction, and sleep disorder; phencyclidine-related disorders, phencyclidine-use disorders selected from dependence and abuse disorder; phencyclidine-induced disorders selected from intoxication, intoxication delirium, psychotic, mood, and anxiety disorder; sedative-, hypnotic- or anxiolytic-related disorders, sedative-use disorders selected from dependence and abuse disorders; sedative-induced disorders selected from intoxication, withdrawal, intoxication delirium, withdrawal delirium, persisting dementia, persisting amnestic, psychotic, mood, anxiety, sexual dysfunction, and sleep disorders; polysubstance-related disorder, vision disorders, and glaucoma; comprising administering to a subject in need thereof a therapeutically effective amount of a salt according to claim 1.

* * * * *